United States Patent [19]

Iwakura et al.

[11] Patent Number: 5,502,020
[45] Date of Patent: Mar. 26, 1996

[54] CATALYST FOR PRODUCTION OF ETHYLENE OXIDE AND PROCESS FOR PRODUCING THE CATALYST

[75] Inventors: Tomoatsu Iwakura; Yukako Kawakatsu, both of Ibaraki, Japan

[73] Assignee: Mitsubishi Petrochemical Co., Ltd., Tokyo, Japan

[21] Appl. No.: 222,592

[22] Filed: Apr. 4, 1994

[30] Foreign Application Priority Data

Apr. 14, 1993 [JP] Japan .................................. 5-087580

[51] Int. Cl.⁶ .............................. B01J 23/04; B01J 23/30
[52] U.S. Cl. .................. 502/317; 502/304; 502/306; 502/308; 502/311; 502/344; 502/348; 549/536
[58] Field of Search ...................... 502/317, 344, 502/348, 304, 306, 308, 311

[56] References Cited

U.S. PATENT DOCUMENTS 4,007,135  2/1977  Hayden et al. ...................... 502/317
5,057,481  10/1991  Bhasin ................................. 502/317

FOREIGN PATENT DOCUMENTS 0172565  2/1986  European Pat. Off. .
0357292  3/1990  European Pat. Off. .

*Primary Examiner*—Anthony Mc Farlane
*Attorney, Agent, or Firm*—Wenderoth, Lind & Ponack

[57] ABSTRACT

A catalyst for the production of ethylene oxide which contains silver, tungsten, cesium and, in some cases, an alkaline metal other than cesium, an alkaline-earth metal, a rare-earth metal, and/or metal selected from Groups I B, II B, III B, IV A, IV B, V A, V B and VI A of the Periodic Table and tellurium. The use of the catalyst of this invention provides high selectivity in the production of ethylene oxide by the vapor contact oxidation of ethylene.

20 Claims, 2 Drawing Sheets

CATALYST FOR PRODUCTION OF ETHYLENE OXIDE AND PROCESS FOR PRODUCING THE CATALYST

BACKGROUND OF THE INVENTION

1. Field of the Invention

This invention relates to a catalyst for the production of ethylene oxide which is used to produce ethylene oxide by the vapor oxidation of ethylene, and to a process for producing the catalyst. More particularly, this invention relates to a catalyst for the production of ethylene oxide in which silver, tungsten, cesium and, in some cases, other additive metals are deposited on a porous carrier.

2. Description of the Prior Art

The catalyst used for producing ethylene oxide on an industrial scale by the vapor contact oxidation of ethylene with molecular oxygen is a silver catalyst. In order to efficiently produce ethylene oxide, there is a strong demand for improved catalysts with highly selective and long-life catalysts being desired. Therefore, while various methods have been proposed in the past, these methods are primarily concerned with a combination of silver as a main active component with alkaline metal etc. as a reaction accelerator, optimization of the mixture ratio, and an improvement in carriers on which those components are to be deposited.

The specifications of GB 1473251 and GB 1512625 describe that high selectivity is obtained by a catalyst in which potassium, rubidium and/or cesium in a specific amount is deposited along with silver on a porous carrier. The specification of GB 1581884 describes that a catalyst containing silver and sodium, potassium, rubidium or cesium in specific amounts can improve the degree of activity and selectivity.

Also, the specification of U.S. Pat. No. 4,690,913 describes that silver grains deposited on a carrier are tiny and uniform and hence are highly active when used as a catalyst, and discloses a catalyst for the production of ethylene oxide in which the loading of silver grains is uniform from the outside surface layer to the inner layer of the catalyst.

On the other hand, when tungsten is used as a reaction accelerator, Japanese Patent Publication No. 61-21701, for example, discloses a catalyst in which silver and an alkaline metal tungstate are deposited on an α-alumina carrier containing a small amount of sodium. In this Publication, however, the amount of tungsten used is limited to the range of high concentration and the catalyst is defined as being effective only when the content of sodium in the carrier is not more than 0.07% by weight. Further, there is no suggestion found as to whether tungsten exhibits a remarkable accelerating effect or not when the amount of tungsten used is small.

The specification of EP 266015-A discloses a catalyst composition containing rhenium and tungsten each in an amount effective for acceleration, as well as silver. This specification describes that tungsten exhibits an accelerating effect in combination with rhenium, but nothing about the accelerating action of tungsten in the absence of rhenium. Further, the specification of EP 357292-A discloses a silver catalyst containing tungsten, an alkaline metal and sulfur. In this specification, however, the addition of sulfur is essential as a component of the catalyst, and it is not apparent whether a catalyst of high performance can be obtained or not in the absence of sulfur.

SUMMARY OF THE INVENTION

According to the present invention, there is provided a catalyst for the production of ethylene oxide from ethylene, the catalyst comprising a porous carrier and at least silver, tungsten and cesium deposited on the carrier, wherein:

(A) loadings of silver, tungsten and cesium are from 5 to 50 by weight, from 5 to 700 ppm, and from 250 to 2000 ppm, respectively;

(B) the silver is deposited on the outside surface of the carrier and on the inner surfaces of the pores of the carrier; (C) silver grains deposited on the carrier have an average diameter in the range of from 0.01 to 0.4 micron;

(D) the loading ($S_A$) of silver on the outside surface layer of the catalyst and the loading ($I_A$) of silver on the innermost layer of the catalyst satisfy the following formula;

$$I_A \geq 0.65\, S_A$$

(E) the tungsten is deposited on the outside surface of the carrier and on the inner surfaces of the pores of the carrier, and the loading ($S_w$) of tungsten on the outside surface layer of the catalyst and the loading ($I_w$) of tungsten on the innermost layer of the catalyst satisfy the following formula;

$$I_w 0.5\, S_w$$

and (F) the cesium is deposited on the outside surface of the carrier and on the inner surfaces of the pores of the carrier, and the loading ($S_c$) of cesium on the outside surface layer of the catalyst and the loading ($I_c$) of tungsten on the innermost layer of the catalyst satisfy the following formula:

$$I_c \geq 0.7\, S_c$$

Also, according to this invention, there is provided a process for producing a catalyst for the production of ethylene oxide from ethylene, which comprises impregnating a porous carrier with an aqueous solution containing at least a silver salt, a tungsten salt, a cesium salt and an amine as a complex forming agent, and heating the carrier with superheated steam to deposit at least silver, tungsten and cesium on the carrier, whereby the catalyst having the features of (A) to (F) above is formed.

DETAILED DESCRIPTION OF THE INVENTION

The catalyst of this invention and the process for producing the catalyst will be described hereunder in more detail.

(Catalyst Composition)

The catalyst of this invention contains silver, tungsten and cesium, described above, as well as in some cases at least one metal (hereinafter also referred to as "additive metal") selected from the group consisting of alkaline metal except cesium, alkaline-earth metal, rare-earth metal, and metals of Groups I B, II B, III B, IV A, IV B, V A, V B and VI A of the Periodic Table based on IUPAC (1970) and tellurium.

In the catalyst of this invention, silver is deposited on the carrier in an amount of from 5 to 50% by weight, preferably from 5 to 25% by weight, based on the total weight of the catalyst. The deposited silver is usually in the form of metal silver on the carrier. Besides silver, the catalyst of this invention further contains tungsten as a reaction accelerator in an amount of from 5 to 700 ppm, preferably from 20 to 650 ppm, based on the total weight of the catalyst and cesium in an amount of from 250 to 2000 ppm, preferably from 250 to 1300 ppm, based on the total weight of the catalyst.

The catalyst of this invention can contain the above-described additive metal so long as the addition does not degrade the performance of the catalyst.

The alkaline metal other than cesium includes lithium, sodium, potassium or rubidium.

The alkaline-earth metal includes beryllium, magnesium, calcium, strontium or barium.

The rare-earth metal includes scandium, yttrium, samarium, cerium, lanthanum, neodymium, praseodymium or europium.

The metal of Group I B of the Periodic Table includes copper or gold.

The metal of Group II B of the Periodic Table includes zinc, cadmium or mercury.

The metal of Group III B of the Periodic Table includes boron, gallium, indium or thallium.

The metal of Group IVA of the Periodic Table includes titanium, zirconium or hafnium.

The metal of Group IVB of the Periodic Table includes silicon, germanium, tin or lead.

The metal of Group V A of the Periodic Table includes vanadium, niobium or tantalum.

The metal of Group V B of the Periodic Table includes phosphorus, arsenic, antimony, or bismuth.

The metal of Group VI A of the Periodic Table includes chromium or molybdenum.

Strictly speaking, the loading of the additive metal differs depending on the kind of metal, but is generally in the range of from 10 to 10,000 ppm, preferably from 10 to 5,000 ppm. The preferable loading for each kind of metal is in the range of from 10 to 3,000 ppm for the alkaline metal and from 10 to 4,000 ppm for metals except the alkaline metal.

(Porous Carrier)

A porous refractory is used as the porous carrier. Examples of the porous carrier are alumina, silicon carbide, titania, zirconia and magnesia. A carrier containing α-alumina as a primary component is suitable. The carrier has a surface area of from 0.6 to 10 $m^2/g$, preferably 0.6 to 5 $m^2/g$, most preferably 0.8 to 2 $m^2/g$. To maintain the strength and to facilitate the impregnating operation while holding such a surface area, the water absorbance of the carrier is preferably from 20 to 50%, and more preferably from 25 to 45 %. The carrier may contain silica.

The carrier is not subjected to any special limitations in regards to its shape, but may have any form such as a sphere, pellet, ring or saddle. From a practical standpoint, however, the ring form is preferred for increasing the effective factor, minimize the differential pressure in the charged condition of the catalyst, and to prevent pulverization of the catalyst during the charging and operation, taking into account the use of the catalyst in a heat exchanger type multi-pipe reactor which is usually employed in synthesis of ethylene oxide. Moreover, the compressive strength of the carrier is preferably not less than 3 kg.

(Catalyst Components)

The silver compound that can advantageously be used to form silver as a catalyst component of the catalyst of this invention may be any compound which forms a complex soluble in an aqueous solvent with an amine, and decomposes at a temperature of not more than 500° C., preferably not more than 300° C., especially preferably not more than 260° C., to deposit silver. Examples of such a silver compound are silver oxide, silver nitrate, silver carbonate and silver carboxylates such as silver acetate and silver oxalate. Of these examples, silver carboxylates are preferred and, in particular, silver oxalate is most preferred.

The amine as the complex forming agent may be any amine which renders the above silver compound soluble in an aqueous solvent. Examples of such an amine include pyridine, acetonitrile, ammonia and amines having 1 to 6 carbon atoms. Preferable examples are ammonia, monoamines such as pyridine and butylamine, alkanolamines such as ethanolamine, and polyamines such as ethylenediamine and 1,3-propanediamine. Especially, the use of ethylenediamine or 1,3-propanediamine is preferred and the combined use of them is most preferred.

The tungsten compound for use in the catalyst of this invention is a compound which is soluble in a suitable solvent. Preferably, the compound is soluble in the solvent that is used to deposit the silver and alkaline metal. Examples of such a tungsten compound are orthotungstic acid, ditungstic acid, paratungstic acid and ammonium salts thereof. In addition, alkaline metal tungstates can also be used.

The alkaline metal compound for use in the catalyst of this invention is a compound which is soluble in a suitable solvent. Preferably, the compound is soluble in the solvent that is used to deposit the silver and alkaline metal. Examples of such an alkaline metal compound include nitrate, hydroxide, halide, carbonate, bicarbonate, oxalate, carboxylate, sulfate, borate, chromate, molybdate and alkoxide of alkaline metal. Specific examples are cesium nitrate, cesium hydroxide, cesium chloride, cesium carbonate, lithium nitrate, lithium hydroxide, lithium chloride, lithium carbonate, lithium oxalate, lithium sulfate, lithium borate, lithium chromate, lithium molybdate, sodium nitrate, sodium carbonate, sodium dicarbonate, sodium acetate, sodium borate, sodium chromate, sodium ethoxide, potassium nitrate and rubidium nitrate.

The alkaline-earth metal compound for use in the catalyst of this invention is a compound which is soluble in a suitable solvent. Preferably, the compound is soluble in the solvent that is used to deposit the silver and alkaline-earth metal. Examples of such an alkaline-earth metal compound include nitrate, hydroxide, halide, carbonate, oxalate, carboxylate, sulfate, chromate, molybdate and alkoxide of alkaline metal. Specific examples are beryllium nitrate, magnesium nitrate, magnesium carbonate, magnesium oxalate, magnesium ethoxide, calcium nitrate, calcium hydroxide, calcium chloride, calcium acetate, calcium sulfate, calcium molybdate, barium nitrate, barium hydroxide, barium chloride, barium sulfate, strontium sulfate, strontium hydroxide, strontium chloride and strontium nitrate.

The rare-earth metal compound for use in the catalyst of this invention is a compound which is soluble in a suitable solvent. Preferably, the compound is soluble in the solvent that is used to deposit the silver and rare-earth metal. Examples of such a rare-earth metal compound include nitrate, hydroxide, halide, carbonate, oxalate, carboxylate, sulfate and alkoxide of rare-earth metal. Specific examples are yttrium nitrate, yttrium chloride, yttrium carbonate, yttrium oxalate, yttrium acetate, yttrium ethoxide, samarium nitrate, samarium chloride, samarium oxalate, cerium nitrate, cerium hydroxide, cerium carbonate, cerium sulfate, lanthanum nitrate, neodymium nitrate, praseodymium nitrate and europium nitrate.

The compound of Group I B metal for use in the catalyst of this invention is a compound which is soluble in a suitable solvent. Preferably, the compound is soluble in the solvent that is used to deposit the silver and Group I B metal. Examples of such a compound of Group I B include nitrate, hydroxide, halide, carbonate, oxalate, carboxylate, sulfate borate, molybdate of Group I B metal and chloroaurate.

Specific examples are copper nitrate, copper chloride, copper hydroxide, copper carbonate, copper oxalate, copper acetate, copper sulfate, copper oxalate, copper molybdate, lithium tetrachloroaurate, sodium tetrachloreaurate, potassium tetracbloroaurate, sodium dichloroaurate, potassium dichloroaurate.

The compound of Group II B metal for use in the catalyst of this invention is a compound which is soluble in a suitable solvent. Preferably, the compound is soluble in the solvent that is used to deposit the silver and Group II B metal. Examples of such a compound of Group II B metal include nitrate, hydroxide, halide, carbonate, bicarbonate, oxalate, carboxylate, sulfate, borate, chromate, molybdate and alkoxide of Group II B metal. Specific examples are zinc nitrate, zinc chloride, zinc carbonate, zinc oxalate, zinc acetate, zinc borate, zinc chromate, zinc molybdate, zinc diethoxide, cadmium nitrate, cadmium hydoxride, cadmium chloride, cadmium carbonate, cadmium molybdate, mercurous nitrate and mercuric sulfate.

The compound of Group III B metal for use in the catalyst of this invention is a compound which is soluble in a suitable solvent. Preferably, the compound is soluble in the solvent that is used to deposit the silver and Group III B metal. Examples of such a compound of Group III B metal include nitrate, hydroxide, halide, carbonate, oxalate, carboxylate, sulfate, borate, chromate, molybdate and alkoxide of Group III B metal. Specific examples are ammonium borate, potassium borate., sodium borate, lithium borate, barium borate, gallium nitrate, gallium hydroxide, gallium chloride, indium nitrate, indium chloride, indium sulfate, indium isopropoxide, thallous nitrate, thallium chloride, thallium oxalate, thallium carbonate, thallium sulfate.

The compound of Group IVA metal for use in the catalyst of this invention is a compound which is soluble in a suitable solvent. Preferably, the compound is soluble in the solvent that is used to deposit the silver and Group IVA metal. Examples of such a compound of Group IVA metal include nitrate, hydroxide, halide, carbonate, sulfate and alkoxide of Group IVA metal, titanate and zirconate. Specific examples are tetraisopropoxy titanium, zirconium nitrate, zirconium hydroxide, zirconium chloride, zirconium sulfate, zirconium tetramethoxide, hafnium chloride, lithium zirconate, sodium zirconate and potassium zirconate.

The compound of Group IVB metal for use in the catalyst of this invention is a compound which is soluble in a suitable solvent. Preferably, the compound is soluble in the solvent that is used to deposit the silver and Group IVB metal. Examples of such a compound of Group IVB metal include nitrate, hydroxide, halide, carbonate, oxalate, carboxylate, sulfate, borate, chromate, molybdate and alkoxide of Group IVB metal, silicate, germanate and stanate. Specific examples are ethyl silicate, lithium germanate, sodium germanate, potassium germanate, tin chloride, tin oxalate, tin acetate, tin sulfate, lithium stannate, sodium stannate, potassium stannate, tin tetraethoxide, lead nitrate, lead hydroxide, lead oxalate, lead borate, lead chromate, lead molybdate and lead isopropoxide.

The compound of Group V A metal for use in the catalyst of this invention is a compound which is soluble in a suitable solvent. Preferably, the compound is soluble in the solvent that is used to deposit the silver and Group V A metal. Examples of such a compound of Group V A metal include hydroxide, halide, oxalate and alkoxide of Group V A metal, vanadate, niobate and tantalate. Specific examples are vanadium chloride, vanadium triethoxide, sodium vanadate, potassium vanadate, calcium vanadate, niobium chloride, niobium oxalate, niobium ethoxide, potassium niobate, tantalum hydroxide, tantalum chloride, tantalum isopropoxide, sodium tantalate and potassium tantalate.

The compound of Group V B metal for use in the catalyst of this invention is a compound which is soluble in a suitable solvent. Preferably, the compound is soluble in the solvent that is used to deposit the silver and Group V B metal. Examples of such a compound of Group V B metal include nitrate, halide, sulfate and alkoxide of Group V B metal, phosphate and hydrogenphosphate. Specific examples are ammonium phosphate, sodium phosphate, potassium phosphate, ammonium hydrogenphosphate, sopdium hydrogenphosphate, potassium hydrogenphosphate, strontium hydrogenphasphate, arsenic chloride, arsenic triethoxide, antimony chloride, antimony sulfate, antimony triethoxide, bismuth nitrate, bismuth chloride and bismuth sulfate.

The compound of Group VI A metal for use in the catalyst of this invention is a compound which is soluble in a suitable solvent. Preferably, the compound is soluble in the solvent that is used to the deposit silver and Group VI A metal. Examples of such a compound of Group VI A metal include nitrate, halide, carboxylate and sulfate of Group VI A metal, chromate and molybdate. Specific examples are chromium nitrate, chromium chloride, chromium acetate, chromium sulfate, ammonium chromate, lithium chromate, sodum chromate, potassium chromate, rubidium chromate, cesium chromate, magnesium chromate, ammonium molybdate, lithium molybdate, sodium molybdate, cesium molybdate, potassium molybdate and calcium molybdate.

The tellurium compound for use in the catalyst of this invention is a compound which is soluble in a suitable solvent. Preferably, the compound is soluble in the solvent that is used to deposit the silver and tellurium meta. Examples of such a tellurium compound include halide, tellurate and tellurite. Specific examples are tellurium chloride, ammonium tellurate, sodium tellurate, potassium tellurate, lithium tellurite, sodium tellurite, potassium tellurite, calcium tellurite and strontium tellurite.

(Preparation of Catalyst)

Any of the above-described compounds can be deposited on the porous carrier in various ways. It is most realistic for the silver compound to be used in the form of an aqueous solution with an amine. The aqueous solution used may have alcohol or the like added.

The concentration of silver in the impregnating solution is selected so that the amount of silver deposited becomes from 5 to 50% by weight based on the finished catalyst. The impregnating operation is carried out in a usual manner. If necessary, the impregnated carrier may additionally be subjected to decompression, heating or spraying. The amine is added in an amount sufficient to complex the silver compound (usually, two amino groups correspond to one silver atom). It is generally safe and preferred that the amine is added in an amount of from 5 to 30% above the equivalent amount required for the formation of the complex. The tungsten compound and/or the alkaline metal compound can be deposited on the carrier at the same time as or before or after the deposition of the silver compound.

The heat treatment after the impregnating operation is carried out by selecting the temperature and the period of time required for silver to deposit on the carrier. At this time, it is best to select such conditions that silver is deposited on the carrier as uniformly as possible in the form of fine grains In the process for producing the catalyst of this invention, silver is deposited on the carrier preferably by bringing the porous carrier impregnated with an aqueous solution containing at least a silver salt, a tungsten salt, a cesium salt and an amine as a complex forming agent into contact with superheated steam at a temperature of not less than 120° C. under the condition that the porous carrier contains at least a part of the aqueous solution. Particularly, it is advantageous that the silver is deposited on the carrier by bringing the porous carrier impregnated with an aqueous solution containing at least a silver salt, a tungsten salt, a cesium salt and an amine as a complex forming agent into contact with superheated steam at a temperature of from 120° to 500° C., preferably from 120° to 300° C., above all from 150° to 260° C., under the condition that the ratio of dryness (removal) of the aqueous medium in the aqueous solution is in the range of from 0 to 70% by weight, preferably from 0 to 50% by weight.

The use of superheated steam is advantageous in making the catalyst components distributed on the carrier uniform and hence improving performance of the catalyst in general. However, it is particularly remarkable that when the catalyst containing silver, tungsten and cesium of this invention is prepared by steam calcination, the catalyst exhibits a high degree of activity and selectivity which cannot be expected from the effect of steam calcination in the prior art.

Superheated steam having a pressure in the vicinity of normal atmospheric pressure is practically feasible as the superheated steam used in this invention from the standpoint of industrial preparation of the catalyst. It has a temperature of from 120° to 500° C., with 120° to 300° C. in particular being preferable and from 150° to 260° C. being especially preferable. The heating time is preferably from about 1 minute to about 3 hours, but is desirably shorter in view of the practical feasibility and performance of the catalyst. Usually, a period of from 3 to 20 minutes is most preferred. The shortest time required is determined depending upon the amount of the impregnated carrier to be heated, the temperature of the steam and the flow speed of the steam. Steam flow speeds of from 0.3 m/sec to 5 m/sec are preferred in view of the performance and practical feasibility of the catalyst produced.

Heating with superheated steam in this invention may be carried out as follows. The impregnated carriers are laid in a single layer or stacked in a multiplicity of layers in the form of a fixed bed or a moving bed, and superheated steam is passed upwardly, downwardly or sideways through the layer or layers. Since all of the entire layers can be heated at a uniform temperature by the superheated steam, there is no non-uniformity of silver distribution among the layers. From a practical viewpoint, the heating of multiple layers is economical. Nitrogen, air, etc. may be included in some amount into the superheated steam. Steam at the outlet contains amines and other decomposition products formed by the decomposition of the silver salt, and to prevent accumulation of these compounds, some amount of steam should be purged. Basically, however, recycling of overheated steam is possible, resulting in the economical heating. For example, 90% of the superheated steam initially fed may be recycled although this value may vary depending upon both the amount of the steam and the amount of the impregnated carrier.

It is preferred in the process for producing the catalyst of this invention that the porous carrier impregnated with the aqueous solution containing the silver salt and the amine as a complex forming agent and optionally with an aqueous solution of a cationic component and/or an anionic component is heated with superheated steam either as such or after removing the excess of the impregnating solution, so that the ratio of dryness (removal) of the aqueous medium in the aqueous solution falls within the range of from 0 to 70% by weight, preferably from 0 to 50% by weight; or the impregnated carrier is dried, for example, in a current of air at a temperature of not less than 100° C. and then heated with superheated stem by the method described above, thereby to deposit silver on the carrier.

The average diameter of the silver grains distributed on the outside surface and the inner surfaces of the pores of the carrier, defined in the above requirement (C) for the catalyst of this invention, can be measured by observing the section of a catalyst particle by a scanning electron microscope. For example, with regard to silver grains clearly observed on a scanning electron micrograph (e.g., magnification 30,000×), the number of silver grains existing in a certain area (e.g., 3 cm×3 cm) of the photograph and the diameters (the shorter diameters when the grains are not spherical) of the silver grains are read, and the total of the diameters read is divided (averaged) by the total number of the grains. This gives the average diameter.

In this invention, the silver grains deposited on the carrier preferably have an average diameter in the range of from 0.01 to 0.4 micron. It is especially preferred that the silver grains which have an average diameter in the range of from 0.01 to 0.09 micron and also have a diameter in the range of from 0.02 to 0.08 micron are present at least in a proportion of 60%, preferably 80%, for all the silver grains.

The loading ($S_A$) of silver on the outside surface layer of the catalyst and the loading ($I_A$) of silver on the innermost layer of the catalyst, defined in the above requirement (D) for the catalyst of this invention, can be determined by gradually shaving off the catalyst of this invention from the outside surface to the inner layer thereof, and measuring the content (weight) of silver per unit weight (for example, 1 gram) of the catalyst so shaven.

In this invention, the outside surface layer of the catalyst denotes a portion having an average weight of about 5 by weight (in the range of about 4–6%) shaven as uniformly as possible from the outside surface of one catalyst (carrier) particle toward its inner layer when the weight of one catalyst particle is taken as 100%. Also, the innermost layer of the catalyst denotes an inner layer (innermost layer) of the catalyst particle which is left after about 60% by weight on an average (in the range of about 50–70%, preferably 55–65%) has been shaven off from the outside surface of the catalyst (carrier) particle toward its inner layer as uniformly as possible.

A simple method of measuring $S_A$ and $I_A$ is to, by way of example, take 30 to 50 catalyst particles, measure their total weight, rotate the catalyst particles in a rotating vessel to shave off the particles from the surface toward the inner layer, and determine $S_A$ and $I_A$ as average values of all the catalyst particles in accordance with the above method.

In the catalyst of this invention, the following relationship is satisfied between the loading ($S_A$) of silver on the outside surface layer of the catalyst and the loading ($I_1$) of silver on the innermost layer of the catalyst:

$$I_A \geq 0.65\ S_A, \text{ preferably } I_A \geq 0.7\ S_A$$

It is evident therefore that, in the catalyst of this invention, the silver grains are very uniformly deposited ranging from the surface layer of the catalyst particle toward its innermost layer.

It is also evident from the average grain diameter specified in the above requirement (C) that, in the catalyst of this invention, the silver grains distributed on the catalyst carrier are very fine and uniform and do not substantially contain large agglomerated masses.

Furthermore, in the catalyst of this invention, at least tungsten and cesium are deposited on the outside surface of the carrier and on the inner surfaces of the pores of the carrier in addition to silver. For these components, it is required that the following formula be satisfied between the loading ($S_w$) of tungsten on the outside surface layer of the catalyst and the loading ($I_w$) of tungsten on the innermost layer of the catalyst;

$$I_w \geq 0.5 S_w, \text{ preferably } I_w \geq 0.6 S_w,$$

and the following formula be satisfied between the loading (Sc) of cesium on the outside surface layer of the catalyst and the loading (Ic) of cesium on the innermost layer of the catalyst:

$$I_c \geq 0.7 S_c, \text{ preferably } I_c \geq 0.8 S_c$$

Note that $S_w$, $I_w$, $S_c$ and $I_c$ can be measured by the same method as the above-described method of measuring $S_A$ and $I_A$ with regard to the distribution of the silver grains in the catalyst.

When the catalyst of this invention contains at least one kind of the above-described additive metal deposited on the outside surface of the carrier and on the inner surface,s of the pores of the carrier, it is especially advantageous that the following formula be satisfied between the loading ($S_x$) of the additive metal on the outside surface layer of the carrier and the loading ($I_x$) of the additive metal on the innermost layer of the carrier:

$$I_x \geq 0.3 S_x, \text{ preferably } I_x \geq 0.4 S_x$$

(Reaction Conditions)

The reaction of converting ethylene into ethylene oxide by using the catalyst of this invention can be performed by a conventional operating procedure. For example, the pressure is from 1 to 35 kg/cm$^2$, and the temperature is from 180° to 300° C., preferably 200° to 260° C. The proportion of ethylene is from 1 to 80% by volume and the proportion of oxygen is from 1 to 20% by volume. Generally, it is preferred to use a fixed proportion, for example from 20 to 70 by volume, of a diluent such as methane. Oxygen can be supplied in the form of air or as industrial oxygen. The addition of a reaction modifier, such as ethylene dichloride, can prevent the formation of hot spots in the catalyst and can serve to improve the performance, especially selectivity, of the catalyst greatly. The preferred amount of ethylene dichloride added is from several ppm to several tens of ppm.

DETAILED EXPLANATION OF EMBODIMENTS OF THE INVENTION

Figure 1:
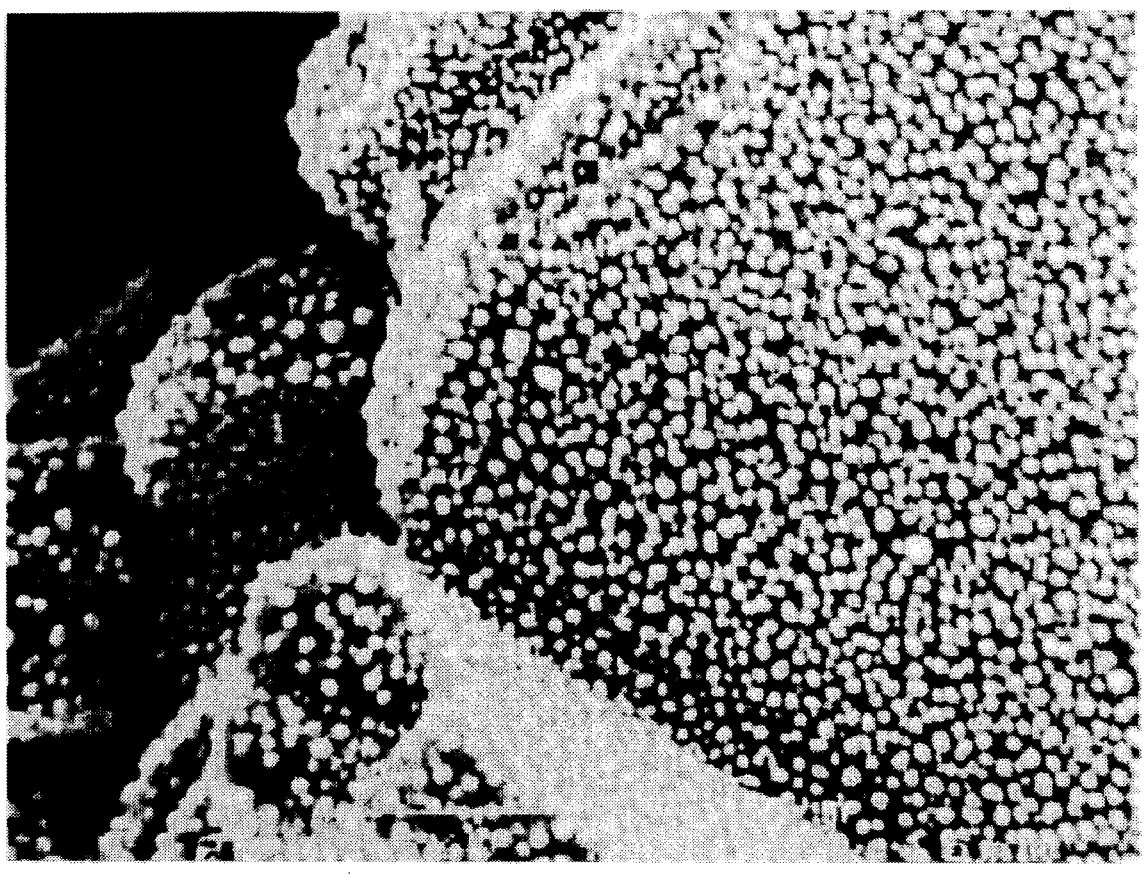
FIG. 1 is a scanning electron micrograph (magnification 30,000×) showing the porous surface of the interior of the catalyst of this invention (Example 1).
Figure 2:
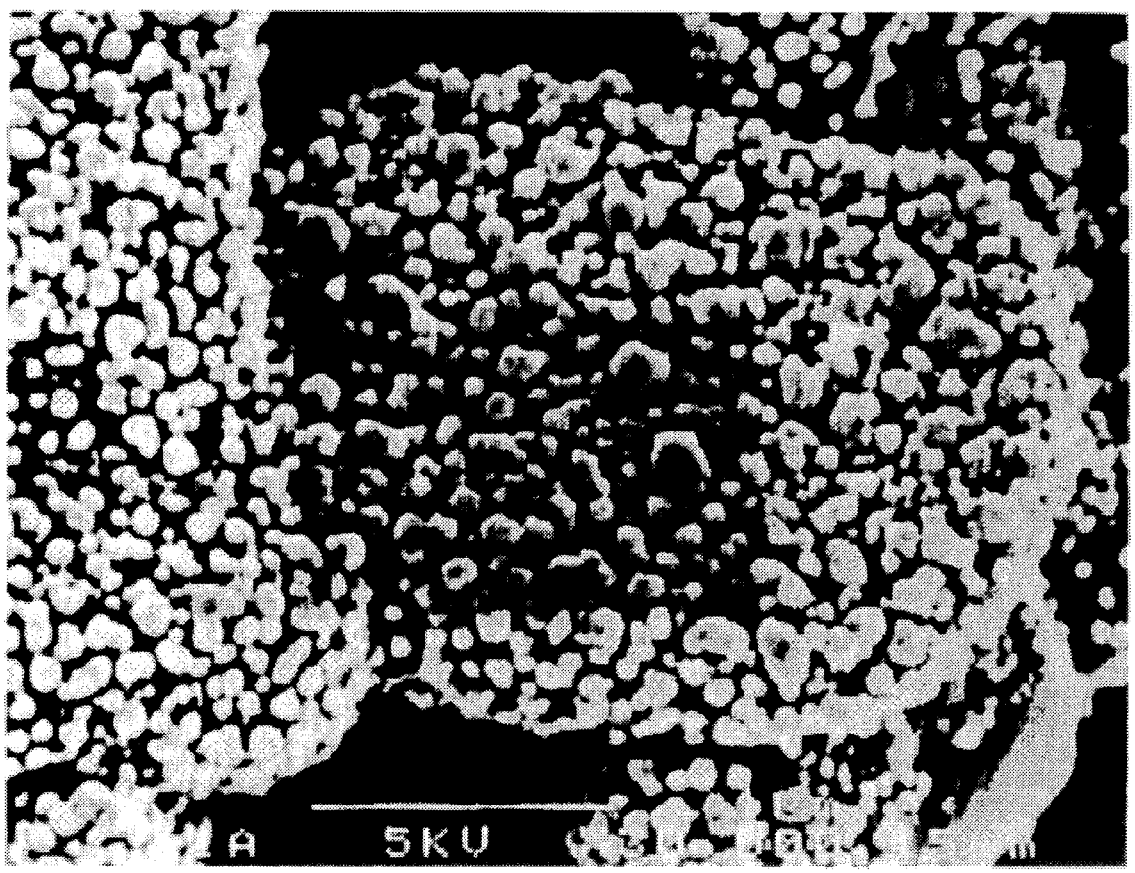
FIG. 2 is a scanning electron micrograph (magnification 30,000×) showing the porous surface of the interior of a control catalyst (Comparative Example 1).

This invention will hereinafter be described in detail with reference to embodiments, but this invention is not limited to these embodiments.

EXAMPLE 1

228g of silver nitrate (AgNO$_3$) and 135 g of potassium oxalate (K$_2$C$_2$O$_4$.H$_2$O) were each dissolved in 1 liter of water separately. The solutions were gradually mixed, while being heated to 60° C., to obtain a white precipitate of silver oxalate. After filtration, the precipitate was washed with distilled water to remove potassium from the precipitate. A part (11.92 g) of the potassium oxalate (K$_2$C$_2$O$_4$ water content of 19.47%) so obtained was dissolved little by little in an amine mixed solution consisting of 3.41 g of ethylenediamine, 0.94 g of propanediamine and 4.40 g of water to prepare a silver-amine complex solution. The silver-amine complex solution was then mixed with 1 ml of aqueous solution containing cesium nitrate (Cs 3.83% by weight) while the mixture was being agitated. Then, 1 ml of aqueous solution containing sodium tungstate Na$_2$WO$_4$.2H$_2$O (W 2.09% by weight) was added to the above mixture.

Thereafter, 50 g of an α-alumina carrier (surface area 1.02 m$^2$/g; water absorbance 34.54%; average diameter of pores 1.9 μm; silica content 3%; ring-like with a size of 8φ ×3φ×8 mm) was immersed in the silver-amine complex solution containing cesium and tungsten to perform the impregnation in an evaporator under reduced pressure and at room temperature. The impregnated carrier was heated with superheated steam of 250° C. for 15 minutes at a flow speed of 2 m/sec to prepare a catalyst in accordance with this invention. The amounts (loadings) of Ag, Cs, W and Na deposited were 12 %, 674 ppm, 368 ppm and 92 ppm, respectively.

The relationship between the loading ($S_A$) of silver on the outside surface layer of the catalyst and the loading ($I_A$) of silver on the innermost layer of the catalyst was given as $I_A \approx 0.71 S_A$. For Cs, W and Na, $I_c \approx 0.84 S_c$, $I_w \approx 0.72 S_w$ and $I_x \approx 0.66 S_x$ were obtained, respectively.

The catalyst prepared by the above method was crushed to a size of from 6 to 10 mesh, and 3 ml of it was filled in a SUS-made reaction tube having an inside diameter of 7.5mm. A reaction gas (composed of 30% of ethylene, 8.5 % of oxygen, 4.0 ppm of vinyl chloride, 6.0% of carbon dioxide and the remainder being nitrogen gas) was passed through the reaction tube under a pressure of 7 kg/cm$^2$G at a GHSV of 4300 h$^{-1}$. The reaction temperature $T_{40}$ (C., bath temperature) at the time when the conversion of oxygen became 40% after one week and the selectivity $S_{40}$ (%) of ethylene oxide based on ethylene at the time when the conversion of oxygen became 40% after one week are shown in Table 1.

EXAMPLE 2

A catalyst was prepared by the same method as Example 1 except that lithium nitrate was also added to the silver-amine complex solution. The amounts (loadings) of Ag, Cs, W, Na and Li deposited were 12%, 674 ppm, 368 ppm, 92 ppm and 34 ppm, respectively.

The catalyst so prepared was subjected to the reaction in a manner similar to Example 1. The results are shown in Table 1.

EXAMPLE 3

A catalyst was prepared by the same method as Example 1 except that the amount of the tungsten solution added to the silver-amine complex solution was reduced to half. The amounts (loadings) of Ag, Cs, W and Na deposited were 12%, 674 ppm, 183 ppm and 46 ppm, respectively.

The catalyst so prepared was subjected to the reaction in a manner similar to Example 1. The results are shown in Table 1.

EXAMPLE 4

A catalyst was prepared by the same method as Example 1 except that the amount of the tungsten solution added to the silver-amine complex solution was reduced to three-quarters. The amounts (loadings) of Ag, Cs, W and Na deposited were 12%, 674 ppm, 92 ppm and 23 ppm, respectively.

The catalyst so prepared was subjected to the reaction in a manner similar to Example 1. The results are shown in Table 1.

EXAMPLE 5

A catalyst was prepared by the same method as Example 1 except that the amount of the tungsten solution added to the silver-amine complex solution was increased by 1.5 times. The amounts (loadings) of Ag, Cs, W and Na deposited were 12%, 674 ppm, 552 ppm and 138 ppm, respectively.

The catalyst so prepared was subjected to the reaction in a manner similar to Example 1. The results are shown in Table 1.

EXAMPLE 6

A catalyst was prepared and subjected to the reaction by the same method as Example 1 except that the impregnated carrier was heated by using superheated steam of 230° C. The results are shown in Table 1.

EXAMPLE 7

A catalyst was prepared by the same method as Example 1 except that lithium nitrate was also added to the silver-amine complex solution and the impregnated carrier was heated by using superheated steam of 230° C. The amounts (loadings) of Ag, Cs, W, Na and Li deposited were 12%, 674 ppm, 368 ppm, 92 ppm and 174 ppm, respectively.

The catalyst so prepared was subjected to the reaction in a manner similar to Example 1. The results are shown in Table 1.

EXAMPLE 8

A catalyst was prepared by the same method as Example 1 except that sodium nitrate was also added to the silver-amine complex solution and the impregnated carrier was heated by using superheated steam of 230° C. The amounts (loadings) of Ag, Cs, W and Na deposited were 12%, 674 ppm, 368 ppm and 115 ppm, respectively.

The catalyst so prepared was subjected to the reaction in a manner similar to Example 1. The results are shown in Table 1.

EXAMPLE 9

A catalyst was prepared by the same method as Example 1 except that sodium carbonate was also added to the silver-amine complex solution and the impregnated carrier was heated by using superheated steam of 230° C. The amounts (loadings) of Ag, Cs, W and Na deposited were 12%, 674 ppm, 368 ppm and 207 ppm, respectively.

The catalyst so prepared was subjected to the reaction in a manner similar to Example 1. The results are shown in Table 1.

EXAMPLE 10

A catalyst was prepared by the same method as Example 1 except that barium nitrate was also added to the silver-amine complex solution and the impregnated carrier was heated by using superheated steam of 230° C. The amounts (loadings) of Ag, Cs, W, Na and Ba deposited were 12%, 674 ppm, 368 ppm, 92 ppm and 685 ppm, respectively.

The catalyst so prepared was subjected to the reaction in a manner similar to Example 1. The results are shown in Table 1.

EXAMPLE 11

A catalyst was prepared by the same method as Example 1 except that calcium nitrate was also added to the silver-amine complex solution and the impregnated carrier was heated by using superheated steam of 230° C. The amounts (loadings) of Ag, Cs, W, Na and Ca deposited were 12%, 674 ppm, 368 ppm, 92 ppm and 400 ppm, respectively.

The catalyst so prepared was subjected to the reaction in a manner similar to Example 1. The results are shown in Table 1.

EXAMPLE 12

A catalyst was prepared by the same method as Example 7. The prepared catalyst was subjected to pretreatment in a current of gas mixture of hydrogen and nitrogen ($H_2$=80 ml/sec, $N_2$=80 ml/sec) for 3 hours at a temperature of 300° C. and then to the reaction in a manner similar to Example 1. The results are shown in Table 1.

EXAMPLE 13

A catalyst was prepared by the same method as Example 1 except that an aqueous solution of lithium tungstate $Li_2WO_4$ was used instead of the aqueous solution of sodium tungstate and the impregnated carrier was heated by using superheated steam of 230° C. The amounts (loadings) of Ag, Cs, W and Li deposited were 12%, 674 ppm, 368 ppm and 28 ppm, respectively.

The catalyst so prepared was subjected to the reaction in a manner similar to Example 1. The results are shown in Table 1.

EXAMPLE 14

A catalyst was prepared by the same method as Example 13 except that lithium nitrate was also added to the silver-amine complex solution. The amounts (loadings) of Ag, Cs, W and Li deposited were 12%, 674 ppm, 368 ppm and 202 ppm, respectively.

The catalyst so prepared was subjected to the reaction in a manner similar to Example 1. The results are shown in Table 1.

EXAMPLE 15

A catalyst was prepared by the same method as Example 1 except that an aqueous solution of cesium chloride was used instead of the aqueous solution of cesium nitrate, an aqueous solution of lithium tungstate was used instead of the aqueous solution of sodium tungstate, and the impregnated carrier was heated by using superheated steam of 230° C. The amounts (loadings) of Ag, Cs, W and Li deposited were 12%, 674 ppm, 368 ppm and 28 ppm, respectively.

The catalyst so prepared was subjected to the reaction in a manner similar to Example 1. The results are shown in Table 1.

EXAMPLE 16

A catalyst was prepared by the same method as Example 1 except that an aqueous solution of cesium carbonate was used instead of the aqueous solution of cesium nitrate, an aqueous solution of lithium tungstate was used instead of the aqueous solution of sodium tungstate, and the impregnated carrier was heated by using superheated steam of 230° C. The amounts (loadings) of Ag, Cs, W and Li deposited were 12%, 787 ppm, 368 ppm and 28 ppm, respectively.

The catalyst so prepared was subjected to the reaction in a manner similar to Example 1. The results are shown in Table 1.

EXAMPLE 17

A catalyst was prepared by the same method as Example 1 except that an aqueous solution of potassium tungstate $KsWO_4$ was used instead of the aqueous solution of sodium tungstate and the impregnated carrier was heated by using superheated steam of 230° C. The amounts (loadings) of Ag, Cs, W and K deposited were 12%, 674 ppm, 368 ppm and 156 ppm, respectively.

The catalyst so prepared was subjected to the reaction in a manner similar to Example 1. The results are shown in Table 1.

Comparative Example 1

A catalyst was prepared and subjected to the reaction by the same method as Example 1 except that air was used instead of superheated steam as the atmosphere for heating the impregnated carrier. The results are shown in Table 1.

The relationship between the loading ($S_A$) of silver on the outside surface layer of the catalyst and the loading ($I_A$) of silver on the innermost layer of the catalyst was given as $I_A \approx 0.64\ S_A$. For Cs, W and Na, $I_c \approx 0.69\ S_c$, $I_w \approx 0.72\ S_w$ and $I_x \approx 0.62\ S_x$ were obtained, respectively.

Comparative Example 2

A catalyst was prepared by the same method as Example 1 except that the amount of the tungsten solution added to the silver-amine complex solution was increased by 3 times. The amounts (loadings) of Ag, Cs, W and Na deposited were 12%, 674 ppm, 1098 ppm and 276 ppm, respectively.

The catalyst so prepared was subjected to the reaction in a manner similar to Example 1. The results are shown in Table 1.

EXAMPLES 18–33

Catalysts were prepared by the same method as Example 1 except that compounds shown in Table 2 were also added to the silver-amine complex solution, respectively and the impregnated carriers were heated by using superheated steam of 230° C. The amounts (loadings) of metals deposited are shown in Table 2, respectively.

The catalysts so prepared were subjected to the reaction in a manner similar to Example 1. The results are shown in Table 2.

EXAMPLE 34

The catalyst was prepared by the same as Example 7 and treated in the reaction gas at a temperature of 190° C. for 16 hours. The catalyst so prepared was subjected to the reaction in a manner similar to Example 1. The results are shown in Table 2.

TABLE 1

| Example No. | $S_{40}$ (%) | $T_{40}$ (°C.) |
|---|---|---|
| 1 | 82.8 | 247 |
| 2 | 82.5 | 235 |
| 3 | 82.1 | 241 |
| 4 | 82.0 | 236 |
| 5 | 82.5 | 252 |
| 6 | 82.6 | 242 |
| 7 | 83.7 | 252 |
| 8 | 83.2 | 252 |
| 9 | 82.3 | 273 |
| 10 | 83.0 | 250 |
| 11 | 82.9 | 235 |
| 12 | 82.9 | 244 |
| 13 | 82.4 | 238 |
| 14 | 82.7 | 249 |
| 15 | 83.1 | 254 |
| 16 | 82.8 | 250 |
| 17 | 82.5 | 255 |
| Comparative Example No. | | |
| 1 | 78.8 | 289 |
| 2 | 75.8 | 306 |

TABLE 2

| Example No. | Compound | Amount of metals deposited | | | | | $S_{40}$ (%) | $T_{40}$ (°C.) |
| | | Ag (%) | Cs(ppm) | W(ppm) | Na(ppm) | X(ppm) | | |
|---|---|---|---|---|---|---|---|---|
| 18 | $Mg(NO_3)_2$ | 12 | 674 | 368 | 92 | Mg 24 | 82.5 | 251 |
| 19 | $Y(NO_3)_3$ | 12 | 674 | 368 | 92 | Y 178 | 82.9 | 246 |
| 20 | $Sm(NO_3)_3$ | 12 | 674 | 368 | 92 | Sm 300 | 82.1 | 246 |
| 21 | $Ti(OCH(CH_3)_2)_4$ | 12 | 674 | 368 | 92 | Tl 96 | 82.3 | 255 |
| 22 | $Zn(NO_3)_2$ | 12 | 674 | 368 | 92 | Zn 130 | 82.4 | 252 |
| 23 | $Cd(NO_3)_2$ | 12 | 674 | 368 | 92 | Cd 225 | 82.4 | 250 |
| 24 | $(NH_4)O.5B_2O_3$ | 12 | 674 | 368 | 92 | B 55 | 82.6 | 249 |
| 25 | $SnCl_4$ | 12 | 674 | 368 | 92 | Sn 237 | 82.1 | 254 |
| 26 | $Si(OC_2H_5)_4$ | 12 | 674 | 368 | 92 | Si 56 | 82.5 | 255 |
| 27 | $Cu(NO_3)_2$ | 12 | 674 | 368 | 92 | Cu 160 | 82.0 | 260 |
| 28 | $Ta_2O_5.nH_2O$ | 12 | 674 | 368 | 92 | Ta 91 | 82.2 | 248 |
| 29 | $(NH_4)_6Mo_7O_{24}$ | 12 | 674 | 368 | 92 | Mo 48 | 82.6 | 258 |

TABLE 2-continued

| Example | | Amount of metals deposited | | | | | | |
|---|---|---|---|---|---|---|---|---|
| No. | Compound | Ag (%) | Cs(ppm) | W(ppm) | Na(ppm) | X(ppm) | $S_{40}$ (%) | $T_{40}$ (°C.) |
| 30 | $Bi(NO_3)_3$ | 12 | 674 | 368 | 92 | Bi 105 | 82.6 | 253 |
| 31 | $KNO_3$ | 12 | 674 | 368 | 92 | K 195 | 82.0 | 257 |
| 32 | $Sr(NO_3)_2$ | 12 | 674 | 368 | 92 | Sr 880 | 82.5 | 244 |
| 33 | $(NH_4)_2TeO_4$ | 12 | 674 | 368 | 92 | Te 128 | 82.7 | 253 |
| 34 | $LiNO_3$ | 12 | 674 | 368 | 92 | Li 174 | 82.5 | 239 |

Note: The solution of $Ti(OCH(CH_3)_2)_4$ in ethanol was used in Example 21.
The solution of $Si(OC_2H_5)_4$ in ethanol was used in Example 26.

As described hereinabove, the catalyst of this invention exhibits high selectivity in the reaction for producing ethylene oxide by the vapor contact oxidation of ethylene, and hence has great industrial value.

What is claimed is:

1. A catalyst for the production of ethylene oxide from ethylene, said catalyst comprising a porous carrier and at least silver, tungsten and cesium deposited on said carrier, wherein:

(A) loadings of silver, tungsten and cesium are from 5 to 50% by weight, from 5 to 700 ppm, and from 250 to 2000 ppm, respectively;

(B) the silver is deposited on the outside surface or said carrier and on the inner surfaces of the pores of said carrier;

(C) silver grains deposited on said carrier have an average diameter in the range of from 0.01 to 0.4 micron;

(D) the loading ($S_A$) of silver on the outside surface layer of said catalyst and the loading ($I_A$) of silver on the innermost layer of said catalyst satisfy the following formula;

$I_A \geq 0.65 S_A$ (E) the tungsten is deposited on the outside surface of said carrier and on the inner surfaces of the pores of said carrier, and the loading ($S_W$) of tungsten on the outside surface layer of said catalyst and the loading ($I_W$) of tungsten on the innermost layer of said catalyst satisfy the following formula;

$I_W \geq 0.5 S_W$ and (F) the cesium is deposited on the outside surface of said carrier and on the inner surfaces of the pores of said carrier, and the loading ($S_C$) of cesium on the outside surface layer of said catalyst and the loading ($I_C$) of tungsten on the innermost layer of said catalyst satisfy the following formula:

$I_C \geq 0.7 S_C$

2. The catalyst according to claim 1, wherein at least one metal selected from the group consisting of alkaline metal except cesium, alkaline-earth metal, rare-earth metal, and metals of Groups I B, II B, III B, IV A, IV B, V A, V B and VI A of the Periodic Table and tellurium is deposited as an additive metal on the outside surface of said carrier and on the inner surfaces of the pores of said carrier, and the loading of said selected metal is from 10 to 10,000 ppm.

3. The catalyst according to claim 2, wherein said alkaline metal is lithium, sodium, potassium or rubidium.

4. The catalyst according to claim 2, wherein said alkaline-earth metal is beryllium, magnesium, calcium, strontium or barium.

5. The catalyst according to claim 2, wherein said rare-earth metal is scandium, yttrium, samarium, cerium, lanthanum, neodymium, praseodymium or europium.

6. The catalyst according to claim 2, wherein said metal of Group I B of the Periodic Table is copper or gold.

7. The catalyst according to claim 2, wherein said metal of Group II B of the Periodic Table is zinc, cadmium or mercury.

8. The catalyst according to claim 2, wherein said metal of Group III B of the Periodic Table is boron, gallium, indium or thallium.

9. The catalyst according to claim 2, wherein said metal of Group IVA of the Periodic Table is titanium, zirconium or hafnium.

10. The catalyst according to claim 2, wherein said metal of Group IVB of the Periodic Table is silicon, germanium, tin or lead.

11. The catalyst according to claim 2, wherein said metal of Group V A of the Periodic Table is vanadium, niobium or tantalum.

12. The catalyst according to claim 2, wherein said metal of Group V B of the Periodic Table is phosphorus, arsenic, antimony or bismuth.

13. The catalyst according to claim 2, wherein said metal of Group VI A of the Periodic Table is chromium or molybdenum.

14. The catalyst according to claim 2, wherein the loading ($S_X$) of said additive metal on the outside surface layer of said carrier and the loading ($I_X$) of said additive metal on the innermost layer of said carrier satisfy the following formula:

$I_X \geq 0.3 S_X$

15. The catalyst according to claim 1 or 2, wherein the silver grains deposited on the inner surfaces of the pores of said carrier have an average diameter in the range of from 0.01 to 0.09 micron, and the silver grains having a diameter in the range of from 0.02 to 0.08 micron are present at least in a proportion of 60% for all the silver grains.

16. A process for producing a catalyst for the production of ethylene oxide from ethylene, which comprises impregnating a porous carrier with an aqueous solution containing at least a silver salt, a tungsten salt, a cesium salt and an amine as a complex forming agent, and heating said carrier with superheated steam to deposit at least silver, tungsten and cesium on said carrier, whereby the catalyst according to claim 1 is formed.

17. The process according to claim 16, wherein said porous carrier impregnated with an aqueous solution containing at least a silver salt, a tungsten salt, a cesium salt and an amine as a complex forming agent is brought into contact with superheated steam at a temperature of not less than 120° C. under the condition that said porous carrier contains said aqueous solution, whereby at least silver, tungsten and cesium are deposited on said carrier.

18. The process according to claim 16, wherein said porous carrier impregnated with an aqueous solution containing at least a silver salt, a tungsten salt, a cesium salt and an amine as a complex forming agent is brought into contact with superheated steam at a temperature of from 120° to 300° C. under the condition that the ratio of dryness (removal) of the aqueous medium in said aqueous solution is in the range of from 0 to 70% by weight, whereby at least silver, tungsten and cesium are deposited on said carrier.

19. The process according to claim 16, wherein said silver salt is silver carboxylate, said tungsten salt is sodium tungstate, lithium tungstate or potassium tungstate, and said cesium salt is cesium nitrate, cesium chloride, cesium carbonate or cesium hydride.

20. The process according to claim 16, wherein said aqueous solution further contains, as an additive metal salt, at least one metal salt selected from the group consisting of an alkaline metal salt except the cesium salt, an alkaline-earth metal salt, a rare-earth metal salt, and metal salts of Groups II B, III B, IVA, IVB, V A, V B and VI A of the Periodic Table and tellurium salt, whereby said additive metal deposited on said carrier.

* * * * *